US00PP33823P3

(12) United States Plant Patent
Schoone

(10) Patent No.: US PP33,823 P3
(45) Date of Patent: Jan. 4, 2022

(54) ***PHALAENOPSIS* PLANT NAMED 'SPLASH GORDON'**

(50) Latin Name: *Phalaenopsis hybrida*
Varietal Denomination: Splash Gordon

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/180,740

(22) Filed: Feb. 20, 2021

(65) Prior Publication Data

US 2021/0267108 P1 Aug. 26, 2021

Related U.S. Application Data

(60) Provisional application No. 63/100,011, filed on Feb. 25, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Phalaenopsis* plant named 'Splash Gordon', characterized by its upright plant habit; moderately vigorous growth habit; strong flowering stems; strong and relatively small leaves; freely flowering habit with typically two inflorescences per plant, each inflorescence with numerous flowers; large white, reddish purple and yellow-colored flowers; and good postproduction longevity.

2 Drawing Sheets

Figure 1:
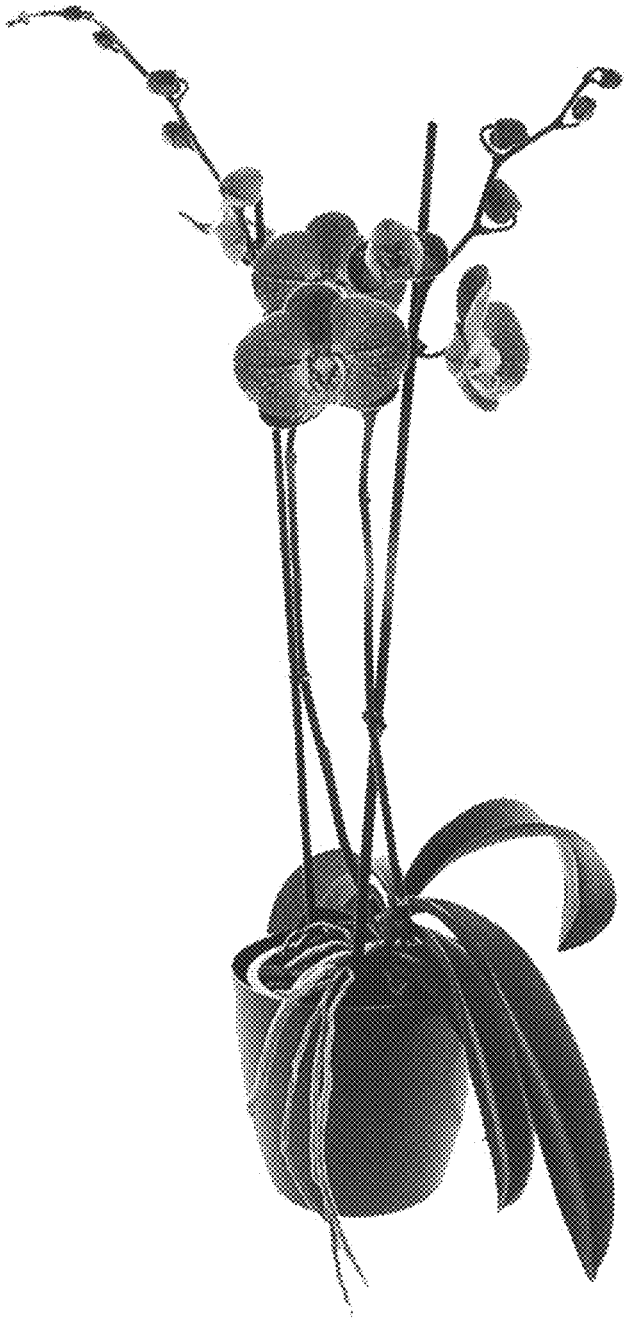

Botanical designation: *Phalaenopsis hybrida.*
Cultivar denomination: 'SPLASH GORDON'.

CROSS-REFERENCED TO CLOSELY-RELATED APPLICATIONS

Title: Varieties of *Phalaenopsis* Plants
Inventor: René Schoone
Filed: Feb. 25, 2020
Ser. No.: 63/100,011
Inventor and Applicant/Assignee hereby claims the benefit of this provisional U.S. Patent Application.

STATEMENT REGARDING PRIOR DISCLOSURES BY INVENTOR/APPLICANT

An European Community Plant Breeder's Rights application for the instant plant was filed by the Applicant/Assignee of the instant application, Floracultura B.V. of Heemskerk, The Netherlands on Sep. 20, 2019, application number 2019/2322. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Splash Gordon'.

The new *Phalaenopsis* plant is a product of a planned breeding program conducted by the Inventor in De Lier, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in October, 2012 in De Lier, The Netherlands of *Phalaenopsis hybrida* 'Pink Twilight', not patented, as the female, or seed, parent with a proprietary selection of *Phalaenopsis hybrida* identified as code number CX 333, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in February, 2016.

Asexual reproduction of the new *Phalaenopsis* plant by in vitro meristem propagation in a controlled environment in Assendelft, The Netherlands since February, 2017 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Splash Gordon'. These characteristics in combination distinguish 'Splash Gordon' as a new and distinct *Phalaenopsis* plant:

1. Upright plant habit.
2. Moderately vigorous growth habit.
3. Strong flowering stems.
4. Strong and relatively small leaves.
5. Freely flowering habit with typically two inflorescences per plant, each inflorescence with numerous flowers.
6. Large white, reddish purple and yellow-colored flowers.
7. Good postproduction longevity.

Plants of the new *Phalaenopsis* can be compared to plants of the female parent, 'Pink Twilight'. Plants of the new *Phalaenopsis* differ primarily from plants of 'Pink Twilight' in flower color as plants of the new *Phalaenopsis* have white, reddish purple and yellow-colored flowers whereas plants of 'Pink Twilight' have soft pink-colored flowers with slightly darker pink-colored stripes.

Plants of the new *Phalaenopsis* can be compared to plants of the male parent selection. Plants of the new *Phalaenopsis* differ primarily from plants of the male parent selection in flower color as plants of the new *Phalaenopsis* have white, reddish purple and yellow-colored flowers whereas plants of the male parent selection have dark red/purple and white-colored flowers.

Plants of the new *Phalaenopsis* can be compared to plants of *Phalaenopsis hybrida* 'Avant Garde', not patented. In side-by-side comparisons, plants of the new *Phalaenopsis* differ primarily from plants of 'Avant Garde' in flower color as plants of the new *Phalaenopsis* have white, reddish purple and yellow-colored flowers whereas plants of 'Avant Garde' have purple/red and white-colored flowers.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Splash Gordon' grown in a container.

Figure 2:
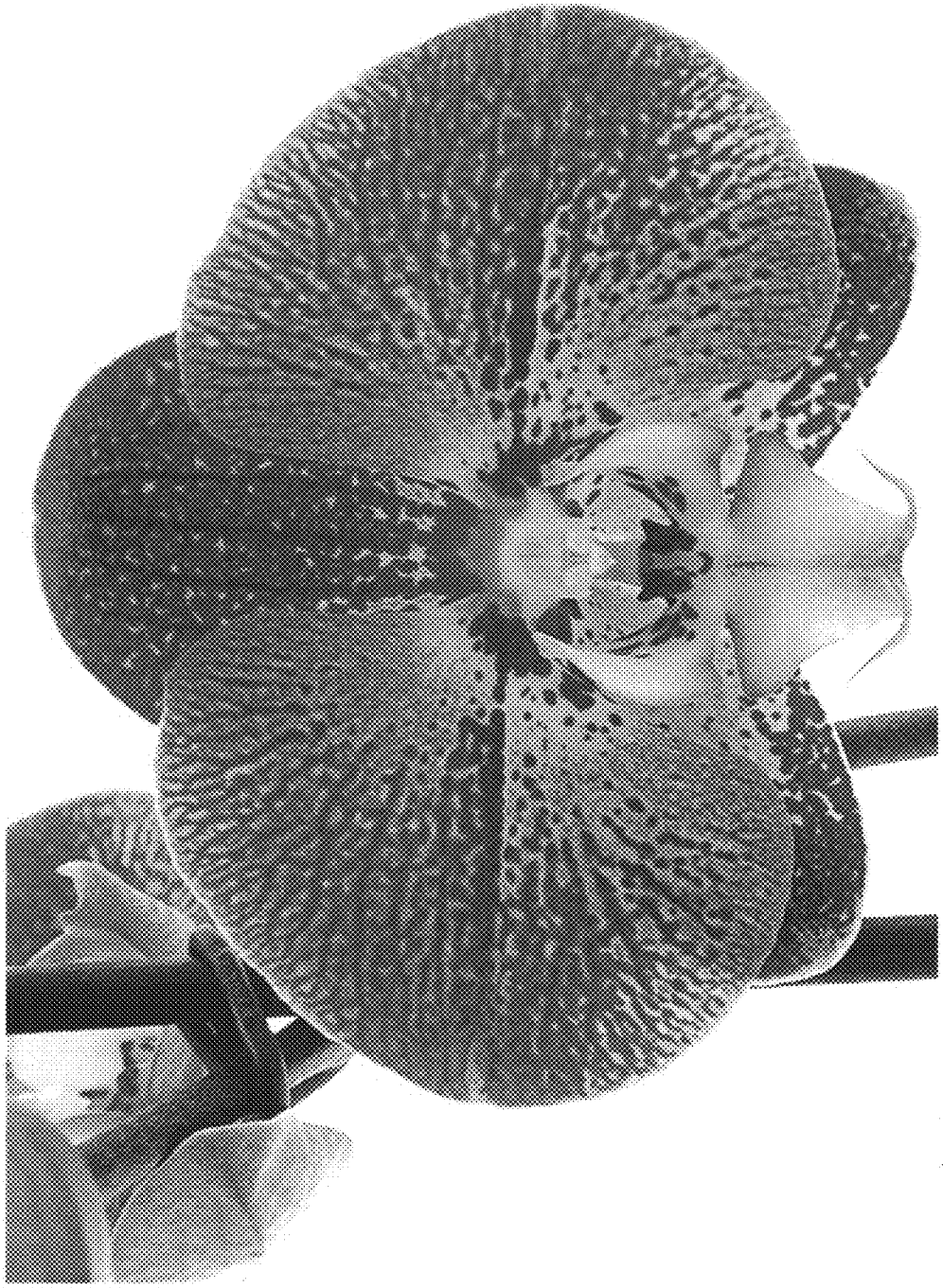

The photograph on the second sheet (FIG. 2) is a close-up view of a typical flower of 'Splash Gordon'.

DETAILED BOTANICAL DESCRIPTION

The aforementioned photographs and following observations and measurements describe plants grown during the early spring in 10-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Splash Gordon'.

Parentage:

*Female parent.*—*Phalaenopsis hybrida* 'Pink Twilight', not patented.

*Male parent.*—Proprietary selection of *Phalaenopsis hybrida* identified as code number CX 333, not patented.

Propagation:

*Type.*—By in vitro meristem propagation.

*Time to initiate roots.*—About two weeks at temperatures about 28° C. to 30° C.

*Time to produce a rooted young plant.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two inflorescences per plant, each inflorescence with numerous flowers; monopodial; moderately vigorous growth habit and moderate growth rate.

*Plant height, substrate level to top of foliar plane.*—About 7.5 cm.

*Plant height, substrate level to top of inflorescences.*—About 45.3 cm.

*Plant diameter or spread.*—About 40.6 cm.

Leaf description:

*Arrangement and quantity.*—Distichous, simple; sessile; about six leaves per plant.

*Length.*—About 20.3 cm.

*Width.*—About 5.6 cm.

*Aspect.*—Outwardly arching.

*Shape.*—Oblanceolate; moderately carinate.

*Apex.*—Unequal acute.

*Base.*—Sheathing.

*Margin.*—Entire; moderately revolute.

*Texture and luster, upper and lower surfaces.*—Smooth, glabrous; very slightly glossy.

*Venation pattern.*—Camptodromous.

*Color.*—Developing leaves, upper surface: Close to NN137B; towards the base and the margins, tinged with close to 200A. Developing leaves, lower surface: Close to 200A slightly tinged with close to N186C. Fully expanded leaves, upper surface: Close to NN137A to NN137B; venation, close to between N186C and 200A. Fully expanded leaves, lower surface: Close to between 146A and 147B; towards the base and the margins, slightly tinged with between N186C and 200A; venation, close to 144A to 144B.

Inflorescence description:

*Appearance and flowering habit.*—Showy zygomorphic flowers arranged on axillary branched racemes; typically two inflorescences per plant; each inflorescence with about ten flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting.

*Flower longevity*.—Long flowering period, individual flowers maintain good substance for about eight weeks on the plant; flowers not persistent.

*Inflorescence length* (*lowermost flower to inflorescence apex*).—About 26 cm.

*Inflorescence width*.—About 13.5 cm.

*Flower buds*.—Height: About 2.1 cm. Diameter: About 1.6 cm by 1.8 cm. Shape: Broadly ovate. Color: Close to 195A; proximally, close to N77B; sepal margins, close to 59A.

*Flower size*.—About 6.7 cm (vertical) by 8.5 cm (horizontal).

*Flower depth*.—About 3.1 cm.

*Petals, quantity and arrangement*.—Three, two lateral petals and one center petal transformed into a labellum.

*Lateral petals*.—Length: About 4.3 cm. Width: About 5.1 cm. Shape: Reniform. Apex: Shallowly emarginate to rounded. Margin: Entire. Texture and luster, upper and lower surfaces: Smooth, glabrous, moderately velvety; matte. Color: When opening, upper surface: Close to N78A to N78C; towards the base, close to 76D; dense variegation, venation and spots, close to between 71A and N79C, N79C and between N79B and N79C. When opening, lower surface: Close to 76B; venation, close to 77B. Fully opened, upper surface: Close to N78C to N78D; towards the base, close to NN155C; dense variegation, venation and spots, close to between N78A and NN78A, N78A and between N79B and N79C; color does not change with development. Fully opened, lower surface: Close to 76B and 77D; venation, close to 77B; color does not change with development.

*Labella*.—Appearance: Tri-lobed with two lateral lobes and a central lobe. Length, lateral lobes: About 1.9 cm. Width, lateral lobes: About 1.4 cm. Length, central lobe: About 3.3 cm. Width, central lobe: About 0.8 cm to 2.2 cm. Shape, lateral lobes: Obovate. Shape, central lobe: Deltoid. Apex, lateral lobes: Obtuse. Apex, central lobe: Emarginate with two short, narrow and recurved cirrose tips, about 1.1 cm in length and about 2 mm in width. Margins, lateral lobes: Shallowly crenate. Margins, central lobe: Entire. Texture and luster, upper and lower surfaces: Smooth, glabrous, moderately velvety; matte. Callosities: Located at the base of the labellum and attachment point of the lateral petals; about 4 mm in length, about 6.5 mm in width and about 6 mm in height. Color: When opening, upper surface: Lateral lobes: Close to NN155B; towards the apex, slightly tinged with close to 76B; towards the base, spots, close to N71A; basal margin, close to 12B with edges, close to 172C. Central lobe: Close to 76C; towards the apex and midvein, close to N78B; towards the base, close to 11B with margin, close to 184B; at the base, proximally (at connection of lobe to column), close to N77A and distally, close to 157A; cirrhose tips, close to N78B to N78D. Callosities: Close to 11C; distally, close to N77A. When opening, lower surface: Lateral lobes: Close to NN155B and 157D; towards the apex, tinged with close to N78C; basal margin, close to 13C with edges, close to 172B to 172C. Central lobe: Close to N78A; towards the basal margins and lateral apices, close to 166B; at the base, proximally (at connection of lobe to column), close to 157A to 157B; cirrhose tips, close to N78D to lighter than N78D. Fully opened, upper surface: Lateral lobes: Close to NN155B; towards the apex, slightly tinged with close to 76B; towards the base, spots, close to N71A; basal margin, close to 12A with edges, close to 172C. Central lobe: Close to 76C; towards the apex and midvein, close to N78B; towards the base, close to 11B with margin, close to 184B; at the base, proximally (at connection of lobe to column), close to N77A and distally, close to 157A; cirrhose tips, close to N78C to N78D. Callosities: Close to 11C; distally, close to N77A. Fully opened, lower surface: Lateral lobes: Close to 155C; towards the apex, tinged with close to N78C; basal margin, close to 12A with edges, close to 172B to 172C. Central lobe: Close to N78A; towards the basal margins and lateral apices, close to 166B; at the base, proximally (at connection of lobe to column), close to 157A to 157B; cirrhose tips, close to N78D to lighter than N78D.

*Sepals*.—Quantity and arrangement: Three, two lower lateral sepals and one upper dorsal sepal. Length, lateral sepal: About 4.2 cm. Width, lateral sepals: About 2.7 cm. Length, dorsal sepal: About 4.2 cm. Width, dorsal sepal: About 3.4 cm. Shape, lateral sepals: Ovate; moderately concave. Shape, dorsal sepal: Broadly elliptic; moderately concave. Apex, lateral sepals: Broadly and bluntly acute. Apex, dorsal sepal: Obtuse. Base, lateral and dorsal sepals: Truncate. Margin, lateral and dorsal sepals: Entire. Texture and luster, lateral and dorsal sepals, upper surface: Smooth, glabrous, velvety; matte. Texture and luster, lateral and dorsal sepals, lower surface: Smooth, glabrous, slightly velvety; slightly glossy. Color, lateral sepals: When opening, upper surface: Close to 76D to lighter than 76D; towards the apex, close to N78B; towards the margins, lighter than 76D; heavily spotted and splashed with close to 59A to darker than 59A; fine reticulate venation, close to N186C; basal blotch, close to 193A to 193B. When opening, lower surface: Close to 195A to 195B; towards the base, tinged with close to N77B; venation, close to 187A. Fully opened, upper surface: Close to 76D to lighter than 76D; towards the apex, close to N78A to N78B; towards the margins, lighter than 76D; heavily spotted and splashed with close to 59A to darker than 59A; fine reticulate venation, close to N186C; basal blotch, close to 193A to 193B. Fully opened, lower surface: Close to 196B; towards the base, tinged with close to N77B; venation, close to 71A. Color, dorsal sepal: When opening, upper surface: Close to 75A to 75B; towards the apex, close to NN78A to NN78B; towards the margins, lighter than 79D; heavily spotted and splashed with close to 59A to darker than 59A; fine reticulate venation, close to N186C. When opening, lower surface: Close to between 199B and 199C; broad margins, close to 76A to 76B; venation, close to N77A. Fully opened, upper surface: Close to 75A to 75B; towards the apex, close to NN78A to NN78B; towards the margins, lighter than 79D; heavily spotted and splashed with close to 59A to darker than 59A and N79C; fine reticulate venation, close to N186C. Fully opened, lower surface: Close to between 182C and 199D; broad margins, close to 76A; venation, close to N77B.

*Peduncles*.—Length: About 53.7 cm. Diameter: About 5 mm. Strength: Strong. Aspect: Upright to about 35° from vertical. Texture and luster: Smooth, glabrous; matte. Color: Close to 200A; fine dots, close to 146C to 146D.

*Pedicels*.—Length: About 3.5 cm. Diameter: About 4 mm. Strength: Moderately strong. Aspect: About 70° from peduncle axis. Texture and luster: Smooth, glabrous; matte. Color: Close to N186D and 187D; proximally, close to between N186C and 200A, and distally, close to 156D with stripes, close to N77B.

*Reproductive organs*.—Androecium: Column length: About 9 mm. Column width: About 7 mm. Column color: Close to NN155D; towards the apex, tinged with close to N78B. Pollinia quantity: Two. Pollinia diameter (per two pollinia): About 2.5 mm. Pollinia color: Close to 23A. Gynoecium: Stigma length: About 3.5 mm. Stigma width: About 4 mm. Stigma shape: Reniform. Stigma color: Close to NN155D. Ovary length: About 8 mm. Ovary diameter: About 2 mm. Ovary color: Close to 145C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Splash Gordon' as illustrated and described.

* * * * *